United States Patent [19]
McGregor et al.

[11] 3,947,457
[45] Mar. 30, 1976

[54] METHOD FOR PREPARING 2,5-DIHALO- AND 2,5,6-TRIHALOPYRIDINES

[75] Inventors: Stanley D. McGregor; Herman O. Senkbeil, both of Midland, Mich.

[73] Assignee: The Dow Chemical Company, Midland, Mich.

[22] Filed: Dec. 27, 1974

[21] Appl. No.: 537,055

[52] U.S. Cl................. 260/290 HL; 260/296 R
[51] Int. Cl.²................... C07D 213/02
[58] Field of Search............... 260/290, 650

[56] References Cited
OTHER PUBLICATIONS
Collins et al., J. Chem. Soc., pp. 167–174 (1971) Sec. C.

Primary Examiner—Harry I. Moatz
Attorney, Agent, or Firm—S. Preston Jones

[57] ABSTRACT

A method for preparing 2,5-dihalo- and 2,5,6-trihalopyridines corresponding to the formula

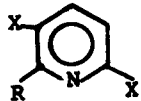

wherein each X independently represents chloro, fluoro or bromo and R represents hydrogen, chloro, fluoro or bromo which comprises reacting a halohydrazinopyridine of one of the formulas

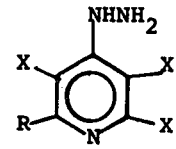

or

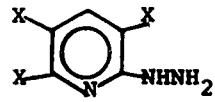

with an excess of an aqueous alkali metal hydroxide in the presence of a reaction medium from the group consisting of loweralkanols of 1 to 4 carbon atoms and loweralkylglycols of 2 to 4 carbon atoms.

11 Claims, No Drawings

METHOD FOR PREPARING 2,5-DIHALO- AND 2,5,6-TRIHALOPYRIDINES

BACKGROUND OF THE INVENTION

Dihalo- and trihalopyridines and especially 2,5-dihalo- and 2,5,6-trihalopyridines are well known bacterials, fungicides and pesticides and in addition these compounds are useful as intermediates in the preparation of other pesticides and antiviral and antibacterial agents. Such uses are taught in many patents including U.S. Pat. Nos. 3,244,586, 1,778,784 and 3,420,833.

These compounds can be prepared by a number of methods including halogen exchange, and high pressure chlorination and bromination processes. Many of the presently employed methods for the preparation of these compounds use pyridine as a starting material and are expensive, or time consuming, or give undesirably low yields. It has become apparent that a method for preparing the 2,5-dihalo and 2,5,6-trihalopyridines from the more readily available tetrahalo- and pentahalopyridines would be advantageous.

Collins et al, J. Chem. Soc., (c); pages 167–174 (1971) teach that halogens ortho and para to the ring nitrogen in pentahalopyridines are reactive with hydrazine hydrate. This reference further teaches the formation of tetrahalo-4-hydroxypyridines from the action of aqueous sodium hydroxide on tetrahalo-4-hydrazino pyridines.

SUMMARY OF THE INVENTION

It has now been found that 2,5-dihalo- and 2,5,6-trihalopyridines corresponding to the formula

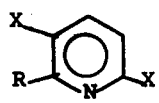

Formula I wherein each X independently represents chloro, fluoro or bromo and R represents hydrogen, chloro or bromo; and more specifically 2,5-dihalo- and 2,5,6-trihalopyridines corresponding to one of the formulas

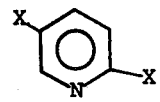 and 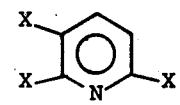

Formula II        Formula III can be prepared in a process which comprises reacting a trihalo-2- or 4-hydrazinopyridine or tetrahalo-4-hydrazinopyridine, respectively with an aqueous alkali metal hydroxide in the presence of a reaction medium from the group consisting of loweralkanols of 1 to 4 carbon atoms and loweralkylglycols of 2 to 4 carbon atoms.

The term "halo" as employed in the present specification and claims designates chloro, bromo and fluoro.

The method of preparation of the present invention can be exemplified by the following reaction schemes:

Reaction Scheme A

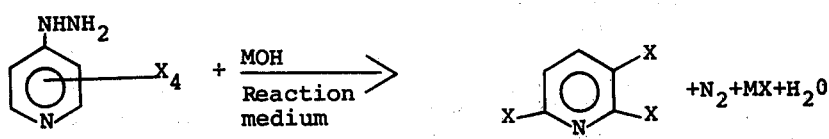

Reaction Scheme B

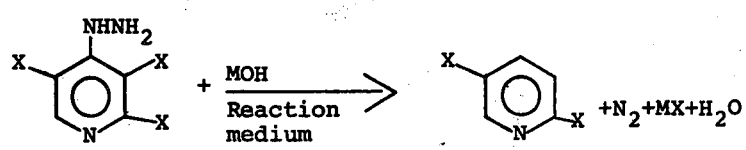

Reaction Scheme C

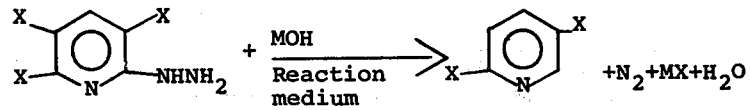

In the above reaction schemes, X is as hereinbefore set forth and M is sodium, potassium, lithium, cesium or rubidium.

As can be seen from the above reaction schemes, during the treatment (reaction) with the alkali metal hydroxide, not only is the hydrazino group removed from the pyridine ring but a halogen atom is also unexpectedly removed.

Representative halopyridine compounds which can be prepared by the method of the present invention include:

2,5-dichloropyridine; 2,5-difluoropyridine; 2,5-dibromopyridine; 2-chloro-5-bromopyridine; 2-chloro-5-fluoropyridine; 2-fluoro-5-chloropyridine; 2-fluoro- 5-bromopyridine; 2-bromo-5-chloropyridine; 2-bromo-5-fluoropyridine; 2,5,6-trichloropyridine; 2,5,6-tribromopyridine; 2,5,6-trifluoropyridine; 2,5-dichloro-6-fluoropyridine; 2,5-dichloro-6-bromopyridine; 2,6-dichloro-5-fluoropyridine; 2,6-dichloro-5-bromopyridine; 2,6-difluoro-5-chloropyridine; 2,6-dibromo-5-chloropyridine and 2,6-difluoro-5-bromopyridine.

In carrying out the above reactions, the trihalo-2- or 4-hydrazinopyridine or tetrahalo-4-hydrazinopyridine reactant is mixed with the loweralkanol or loweralkylglycol reaction medium and alkali metal hydroxide in any suitable fashion and in any order. For example, the pyridine reactant can be first admixed with the reaction medium and this mixture slowly added to the aqueous alkali metal hydroxide or, the pyridine compound reactant can be first admixed with the aqueous alkali metal hydroxide and this mixture added to the reaction medium. The mixture is thereafter heated at a temperature of from about 50°C up to the reflux temperature of the mixture until the reaction is complete. The reaction is usually complete in from about 30 minutes to about 3 hours depending upon the specific halopyridine compound reactant and reaction medium being employed. Upon completion of the reaction, the reaction mixture is cooled and diluted with water and the crude product removed by solvent extraction with a solvent such as methylene chloride, benzene, toluene, chloroform or perchloroethylene. The solvent-crude product mixture is further washed with water, dried and the solvent removed by evaporation. The product can be further purified if desired by conventional techniques including, sublimation, distillation or solvent recrystallization.

Representative trihalo-2- and 4-hydrazino- and tetrahalo-4-hydrazinopyridines which may be employed in the practice of the method of the present invention include among others, 3,5,6-trichloro-2-hydrazinopyridine, 3,5,6-tribromo-2-hydrazinopyridine, 3,5,6-trifluoro-2-hydrazinopyridine, 3,5-dichloro-6-fluoro-2-hydrazinopyridine, 3,5-dichloro-6-bromo-2-hydrazinopyridine, 3,5-difluoro-6-chloro-2-hydrazinopyridine, 2,3,5-trichloro-4-hydrazinopyridine, 2,3,5-trifluoro-4-hydrazinopyridine, 2,3,5-tribromo-4-hydrazinopyridine, 3,5-dichloro-6-fluoro-4-hydrazinopyridine, 3,5-dichloro-6-bromo-4-hydrazinopyridine, 2,3,5,6-tetrachloro-4-hydrazinopyridine, 2,3,5,6-tetrabromo-4-hydrazinopyridine and 2,3,5,6-tetrafluoro-4-hydrazinopyridine.

Representative reaction mediums, i.e. solvents for carrying out the reaction include the loweralkanols such as, for example, methanol, ethanol, propanol, isopropanol, n-butanol, secondary butanol and tertiary butanol and the loweralkyl glycols such as, for example, ethylene glycol, propylene glycol and butylene glycol. The specific reaction medium employed is somewhat dependent on the specific compound being prepared. For example, it has been found that 2,5,6-trichloropyridine is produced in higher yields when isopropanol is employed as the solvent even though the rate of reaction is slow when compared with solvents such as ethanol. On the other hand, ethanol has been found to give high yields and a product of high purity when 2,5-dichloropyridine is produced from 2,3,5-trichloro-4-hydrazinopyridine. While the desired product is produced when either of the above solvents is employed, ethanol is preferred for the production of 2,5-dichloropyridine and isopropanol is preferred for the production of 2,5,6-trichloropyridine.

The amount of reactants employed to carry out this reaction is not critical as some of the product will be formed when employing any proportions. The reaction consumes the reactants, however, in the ratio of one molar equivalent of the alkali metal hydroxide per molar equivalent of the hydrazinopyridine. It is preferred, however, to employ a excess of the alkali metal hydroxide to ensure the complete reaction of the hydrazinopyridine reactant.

DESCRIPTION OF SOME PREFERRED EMBODIMENTS

The following examples illustrate the present invention and the manner by which it can be practiced but, as such, should not be construed as limitations upon the overall scope of the same.

EXAMPLE I — 2,5-DICHLOROPYRIDINE PREPARATION

A mixture consisting of 5 grams (23.5 millimoles) of 2,3,5-trichloro-4-hydrazinopyridine, 10 milliliters (50 millimoles) of 5 Normal (5N) sodium hydroxide and 25 milliliters of ethanol was heated on a stream bath at ~ 75°C. for about 1.25 hours. The reaction mixture was cooled and the mixture separated into an organic and a water phase. To this mixture was added 100 milliliters of water and the organic phase was separated by extraction with methylene chloride. The organic phase was washed with water and dried over magnesium sulfate. The solvent was removed by evaporation under reduced pressure leaving 3.6 grams of a residue. The residue was subjected to sublimation and 2.9 grams of pure white 2,5-dichloropyridine product was recovered (83.3 percent yield of purified material).

Substantially the same procedure was carried out employing 3,5,6-trichloro-2-hydrazinopyridine as the starting pyridine reactant. From the sublimation step, there was obtained 1.9 grams of pure 2,5-dichloropyridine product. The actual yield of the product was ~ 60 percent.

By following the above procedures, and employing the appropriate starting pyridine compounds, the following compounds are prepared:

2,5-Difluoropyridine; 2,5-dibromopyridine; 2-chloro-5-bromopyridine; 2-chloro-5-fluoropyridine; 2-fluoro-5-chloropyridine; 2-bromo-5-chloropyridine; and 2-bromo-5-fluoropyridine.

EXAMPLE II — 2,5,6-TRICHLOROPYRIDINE PREPARATION

To a 10 milliliter solution of 5 Normal sodium hydroxide was added a mixture of 5 grams of tetrachloro-4-hydrazinopyridine in 25 milliliters of isopropanol. The mixture was heated at its boiling point with rapid stirring for 2 hours. The mixture was mixed with 100 milliliters of water and the organic material extracted with methylene chloride. The organic phase was water washed and subjected to sublimation. The 2,5,6-trichloropyridine product was recovered in a yield of 1.85 grams (~ 51 percent of theoretical).

By following the above procedures and employing the appropriate tetrahalo-4-hydrazinopyridine starting material the following compounds are prepared:

2,5,6-tribromopyridine; 2,5,6-trifluoropyridine; 2,5-dichloro-6-fluoropyridine; 2,5-dichloro-6-bromopyridine; 2,6-dichloro-5-fluoropyridine; 2,6-dichloro-5- bromopyridine; 2,6-difluoro-5-chloropyridine; 2,6-dibromo-5-chloropyridine and 2,6-difluoro-5-bromopyridine.

PREPARATION OF STARTING MATERIALS

The trihalo-2- or 4-hydrazinopyridines and tetrahalo-4-hydrazinopyridines can be prepared as taught by Collins et al, cited hereinabove or by the reaction, under reflux conditions, of one mole of 2,3,5,6-tetrahalopyridine, 2,3,4,5-tetrahalopyridine or pentahalopyridine with 2 moles of hydrazin hydrate in the presence of a loweralkanol. After completion of the reaction (~ 2 hours) the reaction mixture is diluted with water and the solid product, as a crude, is separated by filtration. The product is usually purified by recrystallization from a solvent such as methanol, pyridine, benzene, hexane or the like.

While the presently claimed invention is directed to preparation of 2,5-dihalo- and 2,5,6-trihalopyridines from previously prepared trihalo-2-or 4-hydrazinopyridines or tetrahalo-4-hydrazinopyridines, one skilled in the art would recognize the ease with which this process could be commercially adapted to produce a one-step process for the production of the desired compounds from the halopyridine starting material. While no claim is being made for this combined one-step operation, it does illustrate one possible commercial application of the present invention.

In carrying out the above process substantially equimolar amounts of the starting halopyridine compound and a tertiary amine (hydrogen halide acceptor) such as pyridine, triethylamine, trimethylamine or the like and about 1 molar equivalent of hydrazine hydrate in a loweralkanol are refluxed together for about 1–4 hours. To this mixture, while it is still under reflux, is slowly added about 2–3 moles of an alkali metal hydroxide over a period of from 1–4 hours. The mixture is cooled, poured into water and extracted with methylene chloride. The extract is water washed, dried and the solvent removed. The product can be further purified by distillation under reduced pressure. Such a procedure is exemplified below.

EXAMPLE III — 2,5-DICHLOROPYRIDINE

To a reaction flask was added 217 grams (1.0 mole) of 2,3,4,5-tetrachloropyridine, 102 grams (1.0 mole) of triethylamine, 38 grams (0.11 mole) of 95 percent hydrazine and 800 milliliters of ethanol. The mixture was heated under reflux for 3 hours and while still under reflux, 500 milliliters (2.5 moles) of 5 Normal sodium hydroxide was added thereto over a 3 hour period. At the end of this period, the mixture was cooled and poured into 4 liters of water. This mixture was thereafter extracted with four 300 milliliter portions of methylene chloride. The combined methylene chloride extracts were washed with brine, dried over sodium sulfate and the methylene chloride removed by evaporation under reduced pressure. Vacuum distillation of the residue gave a center cut of 135 grams of 2,5-dichloropyridine at a boiling point range of 98°–99°C. at 35 millimeters of mercury. Analysis of the product showed it to be pure 2,5-dichloropyridine melting at 60°–61°C. The overall yield achieved by the process was 91 percent.

What is claimed is:

1. A method for preparing 2,5-dihalopyridine corresponding to the formula:

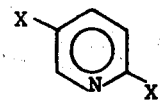

wherein each X independently represents chloro, fluoro or bromo which comprises reacting at a temperature of from about 50°C to the reflux temperature a halohydrazinopyridine of one of the formulas

with an aqueous alkali metal hydroxide in the presence of a reaction medium selected from the group consisting of lower-alkanols of 1 to 4 carbon atoms and loweralkylglycols of 1 to 4 carbon atoms.

2. The method of claim 1 wherein each X represents chloro.

3. The method of claim 1 wherein each X represents fluoro.

4. The method of claim 1 wherein each X represents bromo.

5. The method of claim 1 wherein the halohydrazinopyridine is 2,3,5-trichloro-4-hydrazinopyridine, the alkali metal hydroxide is sodium hydroxide, the reaction medium is ethanol and the 2,5-dihalopyridine is 2,5-dichloropyridine.

6. The method of claim 1 wherein the halohydrazinopyridine is 3,5,6-trichloro-2-hydrazinopyridine, the alkali metal hydroxide is sodium hydroxide, the reaction medium is ethanol and the 2,5-dihalopyridine is 2,5-dichloropyridine.

7. A method for preparing 2,5,6-trihalopyridine corresponding to the formula:

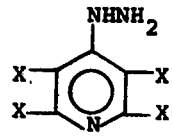

wherein each X independently represents chloro, fluoro or bromo which comprises reacting at a temperature of from about 50°C to the reflux temperature a halohydrazinopyridine of the formula

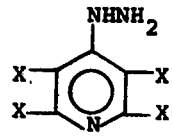

with an aqueous alkali metal hydroxide in the presence of a reaction medium selected from the group consisting of loweralkanols of 1 to 4 carbon atoms and loweralkylglycols of 1 to 4 carbon atoms.

8. The method of claim 7 wherein each X represents chloro.

9. The method of claim 7 wherein each X represents bromo.

10. The method of claim 7 wherein each X represents fluoro.

11. The method of claim 7 wherein the halohydrazinopyridine is tetrachloro-4-hydrazinopyridine, the alkali metal hydroxide is sodium hydroxide, the reaction medium is isopropanol and the 2,5,6-trihalopyridine is 2,5,6-trichloropyridine.

* * * * *

UNITED STATES PATENT AND TRADEMARK OFFICE
CERTIFICATE OF CORRECTION

PATENT NO. : 3,947,457

DATED : March 30, 1976

INVENTOR(S) : Stanley D. McGregor and Herman O. Senkbeil

It is certified that error appears in the above-identified patent and that said Letters Patent are hereby corrected as shown below:

Column 3, line 64, "to give high yields" should read --to give higher yields--;

Column 4, line 25, "stream" should read --steam--;

Column 5, line 11, "hydrazin" should read --hydrazine--.

Signed and Sealed this

Thirteenth Day of July 1976

[SEAL]

Attest:

RUTH C. MASON
*Attesting Officer*

C. MARSHALL DANN
*Commissioner of Patents and Trademarks*